(12) United States Patent
Boyd (10) Patent No.: US 6,761,738 B1
(45) Date of Patent: Jul. 13, 2004

(54) REINFORCED MOLDED IMPLANT FORMED OF CORTICAL BONE

(75) Inventor: Lawrence M. Boyd, Memphis, TN (US)

(73) Assignee: SDGI Holdings, Inc., Wilmington, DE (US)

(*) Notice: Subject to any disclaimer, the term of this patent is extended or adjusted under 35 U.S.C. 154(b) by 0 days.

(21) Appl. No.: 09/664,652

(22) Filed: Sep. 19, 2000

(51) Int. Cl.[7] ............................................. A61F 2/44
(52) U.S. Cl. ............................. 623/17.11; 623/17.16; 623/23.51
(58) Field of Search .................... 623/17.11, 17.15, 623/17.16, 23.47, 23.51, 23.53, 23.48

(56) References Cited

U.S. PATENT DOCUMENTS

| | | | |
|---|---|---|---|
| 4,501,269 A | 2/1985 | Bagby | |
| 4,961,740 A | 10/1990 | Ray | 606/61 |
| 5,026,373 A * | 6/1991 | Ray et al. | 606/61 |
| 5,141,510 A | 8/1992 | Takagi | 623/16 |
| 5,219,363 A | 6/1993 | Crowninshield | 623/23 |
| 5,298,254 A | 3/1994 | Prewett | 424/422 |
| 5,314,478 A | 5/1994 | Oka et al. | 623/17 |
| 5,423,816 A | 6/1995 | Lin | 606/61 |
| 5,423,817 A | 6/1995 | Lin | 606/61 |
| 5,433,718 A | 7/1995 | Brinker | 606/62 |
| 5,458,641 A * | 10/1995 | Ramirez Jimenez | 623/17 |
| 5,507,813 A | 4/1996 | Dowd et al. | 623/16 |
| 5,520,923 A | 5/1996 | Tjia | 424/426 |
| 5,609,635 A * | 3/1997 | Michelson | 623/17.16 |
| 5,645,598 A | 7/1997 | Brosnahan | 623/17 |
| 5,693,100 A | 12/1997 | Pisharodi | 623/17 |
| 5,766,253 A | 6/1998 | Brosnahan | 623/17 |
| 5,814,084 A | 9/1998 | Grivas | 623/16 |
| 5,899,939 A | 5/1999 | Boyce | 623/16 |

(List continued on next page.)

FOREIGN PATENT DOCUMENTS

| | | | |
|---|---|---|---|
| DE | 4409836 A | 9/1995 | |
| EP | 0577179 A | 1/1994 | |
| FR | 2712486 A | 5/1995 | |
| WO | WO91/06266 A | 5/1991 | |
| WO | WO91/11148 | 8/1991 | |
| WO | WO92/14423 | 9/1992 | |
| WO | WO95/00082 | 1/1995 | |
| WO | WO97/23174 A | 7/1997 | |
| WO | WO 99/29271 | 6/1999 | |
| WO | WO 0040177 | 7/2000 | ............. A61F/2/28 |
| WO | WO 01/78798 | 10/2001 | ............. A61L/27/36 |
| WO | WO 01/49219 | 12/2001 | ............. A61F/2/44 |

OTHER PUBLICATIONS

Minns, R.J. "Preliminary Design and Experimental Studies of a Novel Soft Implant for Correcting Sagittal Plane Instability in the Lumbar Spine" *SPINE* vol. 22, No. 16, pp. 1819–1827 (1997).

*Primary Examiner*—Paul B. Prebilic
(74) *Attorney, Agent, or Firm*—Woodard, Emhardt, Moriarty, McNett & Henry LLP (57) ABSTRACT

This invention relates to arthodesis for stabilizing the spine. More specifically, the present invention is directed to an intervertebral spacer formed of a bone material and to methods of treating patients having spinal deformities. The invention provides a spinal implant assembly comprising bone-derived components. The bone-derived components can be formed into modular units that can be assembled to provide a wide variety of implants configurations. In addition, the bone-derived components can form scaffold that can withstand the shear and impact forces necessary to insert the assembled implant into a disc space between adjacent vertebrae. In preferred forms the implants define an open spacer that serves as a depot for receipt of an osteoconductive material. The ostoegenic material is preferably a moldable filler that can form a molded reinforced implant.

19 Claims, 9 Drawing Sheets

U.S. PATENT DOCUMENTS

| | | | | |
|---|---|---|---|---|
| 5,972,368 A | | 10/1999 | McKay | 424/423 |
| 6,019,793 A | * | 2/2000 | Perren et al. | 623/17 |
| 6,025,538 A | | 2/2000 | Yaccarino, III | 623/16 |
| 6,027,744 A | | 2/2000 | Vacanti | 424/426 |
| 6,033,438 A | | 3/2000 | Bianchi | 623/17 |
| 6,037,519 A | | 3/2000 | McKay | 623/16 |
| 6,039,762 A | | 3/2000 | McKay | 623/17 |
| 6,146,420 A | | 11/2000 | McKay | 623/17 |
| 6,190,414 B1 | * | 2/2001 | Young et al. | 623/17.15 |
| 6,200,347 B1 | * | 3/2001 | Anderson et al. | 623/16.11 |
| 6,379,385 B1 | | 4/2002 | Kalas et al. | 623/17.11 |
| 6,423,095 B1 | * | 7/2002 | Van Hoeck et al. | 623/17.16 |
| 2003/0181981 A1 | * | 9/2003 | Lemaire | 623/17.11 |

* cited by examiner

REINFORCED MOLDED IMPLANT FORMED OF CORTICAL BONE

BACKGROUND OF THE INVENTION

The present invention relates to arthodesis for stabilizing the spine. More specifically, the present invention is directed to an intervertebral spacer formed of a bone material and to methods of treating patients having spinal deformities.

Removal of damaged or diseased discs and restoration of disc space height to treat chronic back pain and other ailments are known medical techniques. Implants such as intervertebral spacers are often implanted in the disc space to maintain or reestablish disc space height after removal of all or a portion of the disc. The spacers can be formed of a variety of both resorbable and non-resorbable materials, including, for example, titanium, surgical steel, polymers, composites, and bone. It is also often desirable to promote fusion between the vertebral bodies that are adjacent to the damaged or diseased discs. Typically an osteogenic material is combined with a spacer and inserted in the disc space to facilitate and promote bone growth. While the selection of the implant configuration and composition can depend upon a variety of considerations, for arthodesis it is often desirable to select a resorbable material than does not stress shield the bone ingrowth. Bone and bone-derived components can provide suitable material to prepare the implants. However, bone material acceptable for use in implants is a scarce resource, being derived from limited human tissue donor resources.

Suitable bone or bone-derived material for use in implants, in general, is almost exclusively obtained from allograft and xenograft sources, both which are precious resources. Since intervertebral spacers must withstand the compressive loads exerted by the spine, these implants are often formed from cortical long bones, which are primarily found in the lower limbs and include, for example, femur, fibula, and the tibia bones. The long bones makeup only a fraction of the available bone source. Thus, sources of bone suitable for structural intervertebral spacers are extremely limited. The scarcity of desired donor bone makes it difficult to provide implants having the desired size and configuration for implantation between adjacent lumbar vertebrae, which can require relatively large implants. It is further anticipated that as the population ages there will be an increased need for correction for spinal deformities and a concomitant increase in the demand for bone-derived components. Therefore, these structural bone portions must be conserved and used efficiently to provide implants. The scarcity of suitable bone material has also hindered efforts to design and manufacture varying configurations of suitable implants for arthodesis of the spine. Further, various implant configurations have not been physiologically possible to obtain given the structural and geometrical constraints of available donor bone.

In light of the above-described problems, there continues to be a need to provide suitable implants to facilitate patient treatment. The present invention addresses this need and provides a variety of other benefits and advantages.

SUMMARY OF THE INVENTION

The present invention relates to spinal implants, the manufacture and use thereof. Various aspects of the invention are novel, nonobvious, and provide various advantages. While the actual nature of the invention covered herein can only be determined with reference to the claims appended hereto, certain forms and features, which are characteristic of the preferred embodiments disclosed herein, are described briefly as follows.

In one form, the invention provides an implant for promoting bone fusion between adjacent vertebral bodies. The implant has a longitudinal axis and comprises an assembly of cortical bone-derived components. The components are comprised of a first strut having a first bone-engaging portion and an opposite second bone-engaging portion. A first impact surface is disposed between the first bone-engaging portion and the second bone-engaging portions. The bone-derived components also include a second strut spaced from the first strut. The second strut has a third bone-engaging portion and an opposite fourth bone-engaging portion. A second impact surface is disposed between the third and fourth bone-engaging portions. The components also include an elongate cross-member that extends from the first strut to the second strut. The second strut in cooperation with the first strut defines an internal space. In one embodiment the implant can be provided as an open cage. An osteogenic material can be combined with the implant. The osteogenic material can be interposed between the first and second strut. Preferably, the osteogenic material is provided to be formed within the internal space and/or adherent to at least one of a first strut, the second strut, and the cross-member. The osteogenic material can also be adapted to be moldable to provide a semi-rigid shaped component.

In alternative forms, the first and second strut can be defined by substantially planar walls that can be adapted to restore normal disc height and/or provide correct lordosis of the spine. The first and second strut can include opposite bone-engaging portions that are separated from each other at a first end of the strut by a distance $D_1$ and wherein the opposite bone-engaging uniformly taper to a second distance $D_2$ at a second end of the strut, such that $D_1$ is greater than $D_2$. Alternatively, the bone-engaging portions can define an arcuate surface wherein the opposite bone engaging portions separate from each other at a maximum distance at a point located between the first and the second end on the respective strut. In still yet other embodiments, the first and second struts can define curved wall portions that approximate the medullary canal of a long bone.

In another form, the present invention provides an implant for promoting bone fusion. The implant has a longitudinal axis and comprises an assembly of cortical bone-derived components. The components comprise a first strut having a first bone-engaging portion and an opposite second bone-engaging portion. The first strut also includes a first slot formed therein and extending from the first bone-engaging portion. The first slot has a first internal wall portion and opposing second internal wall portion and an internal end wall portion therebetween. The implant assembly also comprises a second strut that has a third bone-engaging portion and an opposite fourth bone-engaging portion. The second strut also has a second slot formed therein and extending from the third bone-engaging portion. The second slot includes a first internal wall portion and opposing second internal wall portion and internal end wall portion therebetween. The first slot is adapted to receive a portion of the second strut, and the second slot on the second strut is adapted to receive a portion of the first strut to interengage the first and second strut to form the implant assembly. When thus configured, the implant can be adapted to be inserted in the intervertebral space or, alternatively, the implant can be sized to provide a replacement for a vertebral body.

The present invention also provides a method of treating a spinal deformity. The method comprises surgically preparing a intervertebral space between adjacent endplates of adjacent vertebrae and inserting an implant into the prepared space. The implant comprises a first strut having a first bone-engaging portion, an opposite second bone-engaging portion and a first impact surface disposed therebetween, a second strut spaced from said first strut, said second strut having a third bone-engaging portion, an opposite fourth bone-engaging portion, and a second impact surface disposed therebetween, said second strut in cooperation with said first strut defining an internal space, and a cross-member extending from the first strut to the second strut into the intervertebral space.

In yet another form the present invention provides other methods for treating spinal deformities. These methods include surgically preparing a patient to receive a spinal implant; and implanting an implant comprising of an assembly of cortical bone-derived components. The cortical bone-derived components include: a first strut having a first bone-engaging portion and a opposite second bone-engaging portion, said first strut having first slot formed therein, and a second strut having a third bone-engaging portion and a opposite fourth bone-engaging portion, said second strut interengaging said first strut to form the implant.

Further objects, features, aspects, forms, advantages and benefits shall become apparent from the description and drawings contained herein.

DETAILED DESCRIPTION OF THE INVENTION

For the purposes of promoting an understanding of the principles of the invention, reference will now be made to the embodiments illustrated herein and specific language will be used to describe the same. It will nevertheless be understood that no limitation of the scope of the invention is thereby intended. Any alterations and further modifications in the described implants or methods, and any further applications of the principles of the invention as described herein, are contemplated as would normally occur to one skilled in the art to which the invention relates.

The present invention provides a spinal implant that can be assembled from individual bone-derived components. In one form, the individual components can be relatively small, and yet the assembled bone implant can be a larger structure exhibiting suitable strength to withstand the compression loading exerted by a spinal column. The components can be derived from donor bone, such as cortical allograft bone. In addition, the components can be formed as modular pieces having uniform size and shape to facilitate manufacture of the spinal implants. For example, the implant can be provided in selected dimensions and configurations to maintain disc height, correct lordosis, kyphosis or other spinal deformities. In other forms, the spinal implant provides a bone construct that can serve as reinforcing scaffolding for a variety of osteogenic materials to facilitate bone fusion. Thus, this invention provides efficient use of the precious donor bone material and yet allows for the manufacture of a wide variety of implant configurations.

Figure 1:
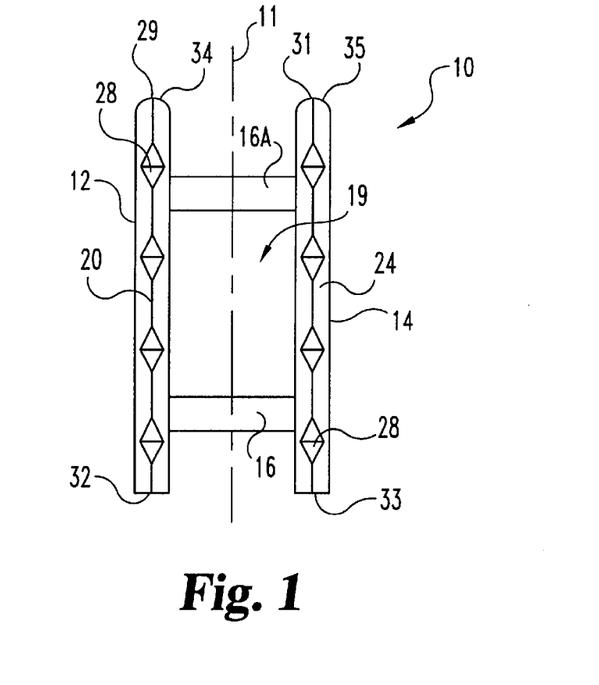
FIG. 1 is a plan view of one embodiment of an implant assembly according to the present invention.

FIG. 1 is a plan view of one embodiment of a spinal implant 10 for use in the present invention. Implant 10 defines a longitudinal axis 11 and includes a first strut 12, a second strut 14 spaced from first strut 12, and cross-member 16 extending therebetween. First strut 12 and second strut 14 are each positioned to lie in a plane substantially parallel to longitudinal axis 11. Implant 10 includes at least one additional cross-member 16A connecting first strut 12 and second strut 14. It is understood that in alternative embodiments implant 10 can have one or a plurality of cross-members connecting first strut 12 to second strut 14.

Figure 2:
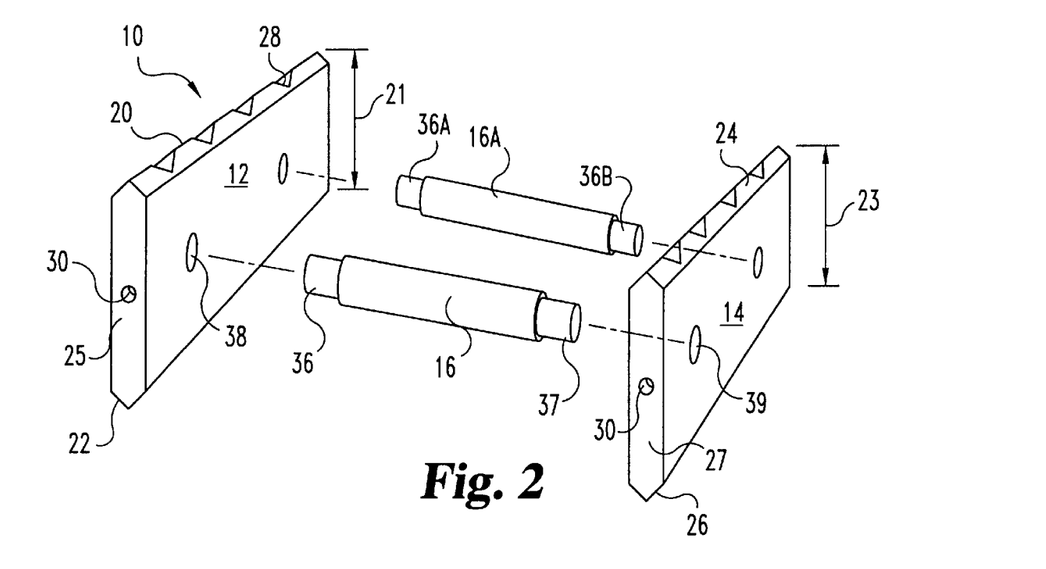
FIG. 2 is an exploded view of the implant assembly illustrated in FIG. 1.

Referring additionally to FIG. 2, which is an exploded view of the implant assembly 10 depicted in FIG. 1, first strut 12 is illustrated as having a substantially rectangular configuration.

First strut 12 includes a first bone-engaging portion 20 and an opposite second bone-engaging portion 22 spaced from the first bone-engaging portion 20 by a first distance illustrated by reference line 21, and which can be selected to be equal to $D_1$. First bone-engaging portion 20 and second bone-engaging portion 22 can be provided to include anti-retropulsion structures 28. In the illustrated embodiment, first bone-engaging portion 20 is provided with a plurality of notches 28 formed therein. Notches 28 provide a mechanical interlock with the adjacent vertebral bone endplates and prevent retropulsion of the implant from the intervertebral space. First bone-engaging portion and/or second bone-engaging portion can also be configured with ridges, spikes, and the like to inhibit retropulsion from the disc space. Alternatively, first bone-engaging portion 20 and second bone-engaging portion 22 can be provided as a substantially smooth or uniformly linear surface. It is understood by those skilled in the art that the exact configuration of first strut 12 can be provided in a variety of configurations, which can be selected to impart a desired corrective effect on a spinal column or portion thereof.

Second strut 14 can be provided substantially as described for first strut 12. Second strut 14 includes a third bone-engaging portion 24, an opposite fourth bone-engaging portion 26. Second strut 14 can include the same structural components as described for first strut 12, including anti-retropulsion structures 28. Third bone-engaging portion 24 is spaced from fourth bone-engaging portion 26 by a second distance represented by reference line 23, which can be selected to be $D_2$. In the illustrated embodiment for implant 10, $D_1$ is substantially equal to the $D_2$. In alternative embodiments, the first distance does not have to equal the second $D_2$. Thus, $D_1$ and $D_2$ individually can be selected to restore and/or maintain desired disc space height between adjacent vertebrae including cervical, thoracic and lumbar vertebrae. Preferably, $D_1$ and $D_2$ are selected to range between about 5 mm and about 20 mm. More preferably, $D_1$ and $D_2$ are selected to range between about 10 mm and about 15 mm.

Figure 7:
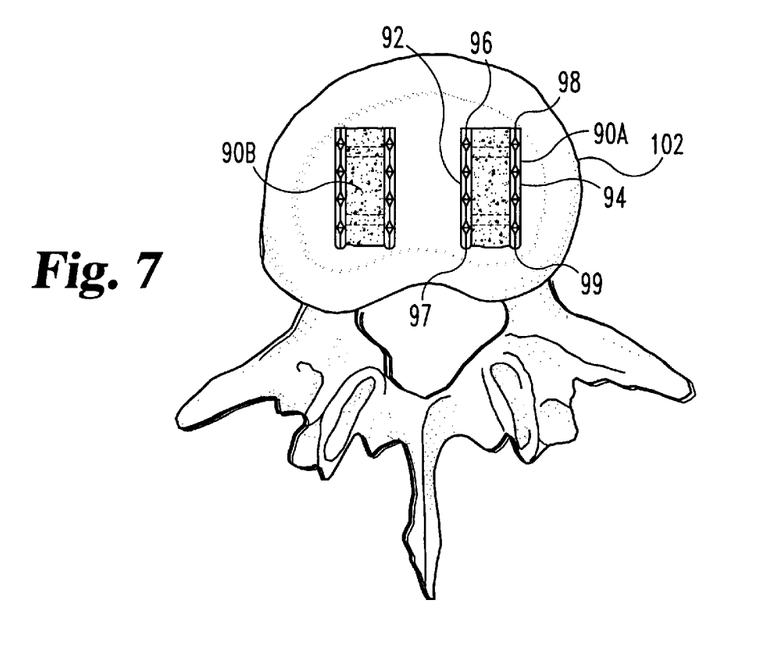
FIG. 7 is a top view of a vertebral body illustrating the bi-lateral placement of a pair of implant assemblies provided in accordance with the present invention.

Second strut 14 is spaced from first strut 12. The distance second strut 14 is spaced from first strut 12 can be varied depending upon the desired use and/or desired site for implantation of the resulting implant assembly. For example, second strut 14 can be spaced from first strut 12 to provide a single implant assembly that is sized to substantially extend the lateral width of a disc space. Alternatively, implant 10 can be sized to allow the bi-lateral placement of a pair of implants within the disc space as illustrated in FIG. 7.

First strut 12 includes impact surface 25 positioned substantially orthogonal to longitudinal axis 11. The impact surface can be disposed between first bone-engaging portion 20 and second bone-engaging portion 22. Similarly second strut 14 includes impact surface 27 also positioned substantially orthogonal to longitudinal axis 11. Impact surfaces 25 and 27 can define a thickened wall portion of struts 12 and 14. Impact surfaces 25 and 27 are adapted to withstand impact forces necessary to drive implant 10 into a disc space. Further, impact surface 25 and 27 can be provided with a surface to facilitate driving implant 10 into a disc space. For example, surfaces 25 and 27 can be roughened, knurled or ridged to maintain static contact between an insertion tool (not shown) and implant 10.

First strut 12 terminates in a first end 32 and at an opposite second end 34. Similarly, second strut 14 terminates at a first end 33 and at an opposite second end 35. In one form, first ends 32 and 33 define impact surfaces 25 and 27, respectively. Further, first ends 32 and 33 are configured to include tool engaging apertures 30 to engage counterpart structures on implant holders and/or insertion tools (not shown). Apertures 30 can include a uniformly smooth bore, a tapered bore or, alternatively, a threaded bore portion. Preferably, tool-engaging portions 30 facilitate insertion of the implant into the disc space and inhibit lateral movement of the implant during insertion. In the illustrated embodiment, second ends 34 and 35 include curved surfaces 29, 31, respectively, to facilitate and ease insertion of implant 10 into the disc space.

Figure 26:
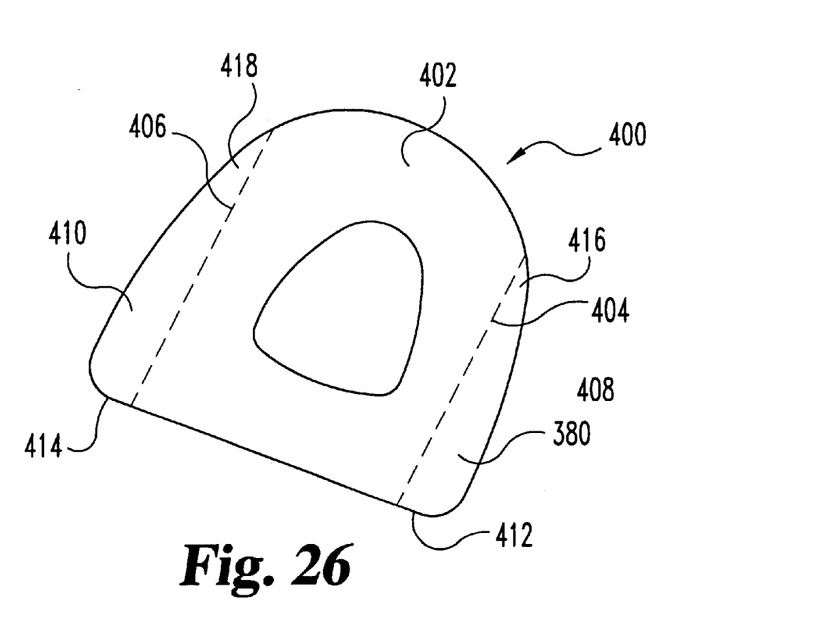
FIG. 26 is a schematic illustrating the selection of a bone portion from a cross-section of a femur.

In a preferred form, first strut 12 and second strut 14 can be provided as modular units that can be coupled via at least one cross-member. The modular units can be obtained by uniform cutting and machining of donor bone. Further, the donor bone can be bone remnants obtained after manufacture of implant configurations as illustrated in FIG. 26 and discussed more fully below. This provides efficient use of precious donor bone resources. The modular units can be of preselected configuration and dimensions. Preferably struts 12 and 14 are provided in configurations to facilitate bone fusion and provide correct lordosis, kyphosis and other spinal deformities.

In the illustrated embodiment, cross-member 16 and cross-member 16A extend from first strut 12 through interior area 19 to second strut 14. In alternative embodiments, cross-members 16 and/or, 16A can be engaged to first strut 12 and second strut 14 about their respective periphery, for example, proximal to first ends 32 and 33 or to second ends 33 and 35. When cross-member 16 or 16A is positioned proximal to first ends 32 and 33, the cross-members can also be adjacent impact surfaces 25 and 27, respectively.

Cross-member 16 includes a proximal end 36, which is capable of engaging first strut 12. In the illustrated embodiment, proximal end 36 engages in aperture 38 of first strut 12. Cross-member 16 also includes a distal end 37, which is capable of engaging with strut 14 via aperture 39. Similarly, cross-member 16A includes a proximal end 36A and a distal end 37A. Proximal end 36A is provided to engage first strut 12, and distal end 37A is provided to engage strut 14. Cross-member 16 and second cross-member 16A are adapted to engage in first strut 12 and second strut 14 to provide an assembled implant that is capable of withstanding the shear and impact forces needed to drive the implant assembly into the intervertebral space. Cross-member 16 is illustrated as a cylindrical rod. In alternative forms, cross-member 16 can be configured as a shaft having a square, rectangular, triangular or ovoid cross-section. Further, it will be understood by those skilled in the art that cross-members 16 and 16A are adapted to engage a first and second strut 12 and 14, respectively, in a variety of configurations, which are discussed in more detail below.

Implant 10 can be configured as an open cage vertebral implant. The open cage vertebral implant provides a depot for-receipt of an osteoconductive/inductive filler. Further, when the implant includes a filler and is sized to be received within a prepared disc space, implant 10 provides structural support to maintain disc height yet allow broad surface area and intimate contact between the filler and bone tissue of the vertebral end plates.

Figures 3, 4:
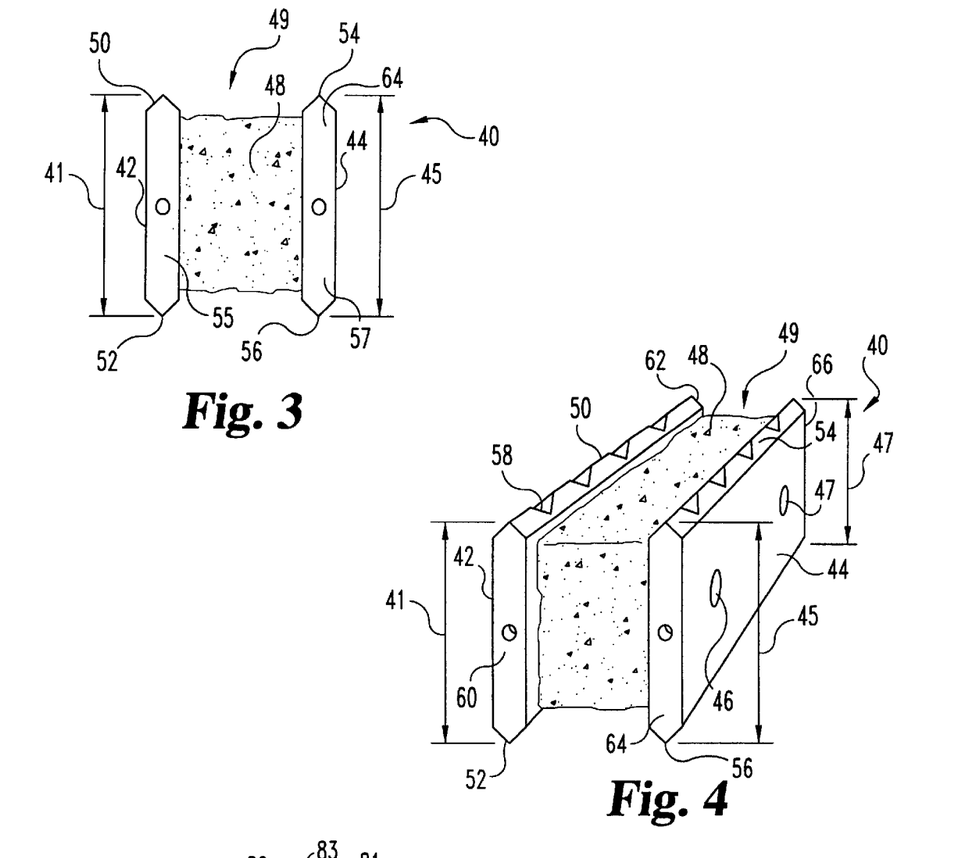
FIG. 3 is an elevated end view of a lordotic implant assembly including an osteogenic material.
FIG. 4 is a perspective view of the implant assembly depicted in FIG. 3.

FIGS. 3 and 4 are illustrations of implant assembly 40 including an osteogenic material 48. Implant assembly 40 includes a first strut 42, second strut 44 and cross-members 46 and 47. First strut 42 and second strut 44 define an interior space 49 therebetween. First strut 42 includes a first bone-engaging portion 50, an opposite bone-engaging portion 52, and a first impact surface 55 therebetween. Similarly, second strut 44 includes a third bone-engaging portion 54, an opposite fourth bone-engaging portion 56, and a second impact surface 57 therebetween. First strut 42 and second strut 14 include anti-retropulsion structures 58 formed therein. In the illustrated embodiment, osteogenic material 48 is deposited between a first strut 42 and second strut 44, substantially filling the entire interior space 49. The osteogenic material 48 can be provided as a moldable material that adheres to the scaffolding defined by struts 42, 44 and optionally cross-members 46 and 47. Osteogenic material 48 also can be provided in sufficient amounts and in a form to extend beyond first and third bone-engaging portions 50 and 54, respectively, and/or second and fourth bone-engaging portions 52 and 56, respectively. Preferably the compressed osteogenic material can bear a portion of the load exerted on the implant assembly 40 by the spinal column. In alternative embodiments, first strut 42 and second strut 44 can be substantially surrounded or embedded in an osteogenic material so the osteogenic material substantially surrounds struts 42 and 44.

First strut 42 includes a first end 60 and an opposite second end 62. First bone-engaging portion 50 is spaced from second bone-engaging portion 52 proximate to first end 60 by first distance illustrated by reference line 41, which can be selected to equal $D_1$. Similarly, first bone-engaging portion 50 is separated from second bone-engaging portion 52 proximal to second end 62 by a third distance, which can be selected to equal $D_3$ (not shown). Second strut 44 includes a first end 64 and an opposite second end 66. Third bone-engaging portion 54 is separated from fourth bone-engaging portion 56 proximal to first end 64 by a second distance illustrated by reference line 45, which can be selected to equal $D_2$. Similarly, third bone-engaging portion 54 is separated from fourth bone-engaging portion 56 proximal to second end 66 by a fourth distance illustrated by reference line 67, which can be selected to equal $D_4$. The values for $D_1$, $D_2$, $D_2$ and $D_4$ can be individually selected to provide an implant assembly capable of achieving a desired orthopedic result.

In one form, first strut 42 has a height adjacent to first end 60 defined by distance $D_1$ and a height adjacent to second end 62 defined by $D_3$. Preferably, but not required, when so provided, first strut 12 tapers uniformly from the height $D_1$ adjacent first end 60 to the height $D_3$ adjacent second end 62. Similarly, second strut 44 can be configured to have a height adjacent to first end 64 defined by $D_2$ and a height adjacent to second end 66 defined by $D_4$ smaller than $D_2$. Second strut can also be provided to uniformly taper in height from first end 64 to second end 66. Further in selected forms $D_2$ can be selected to be less than $D_1$, and $D_4$ can be selected to be less than $D_3$.

Figure 5:
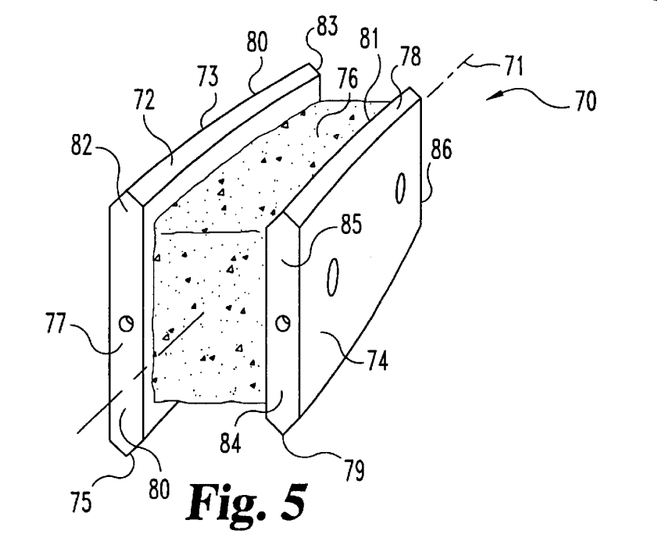
FIG. 5 is a perspective view of an alternate embodiment of an implant assembly including an osteogenic material for use in the present invention.

FIG. 5 is a perspective view of an implant assembly 70. Implant assembly 70 is illustrated as an elongate spacer defining a longitudinal axis 71 and including a first strut 72, a second strut 74 and an osteogenic material 76 interposed therebetween. First strut 72 includes a first bone-engaging portion 73, an opposite second bone-engaging portion 75, and a first impact surface 77 positioned therebetween. Second strut 74 includes a third bone-engaging portion 78 and an opposite fourth bone-engaging portion 79 and impact surface 84 disposed therebetween. Opposite bone-engaging portions extend from a first end 85 to a second end 86 on strut 74. First bone-engaging portion 73 includes an arcuate edge 80 extending substantially parallel to longitudinal axis 71, and third bone-engaging portion 78 includes second arcuate edge 81 extending substantially parallel to longitudinal axis 71. Similarly, second bone-engaging portion 75 and fourth bone-engaging portion 79 also, but are not required to, include arcuate edges (not shown). The first and second struts include pairs of opposite bone-engaging portions, 73, 75, 78 and 79 that are separated from each other at a maximum distance at a point between the first and second ends of the respective struts.

Figure 6:
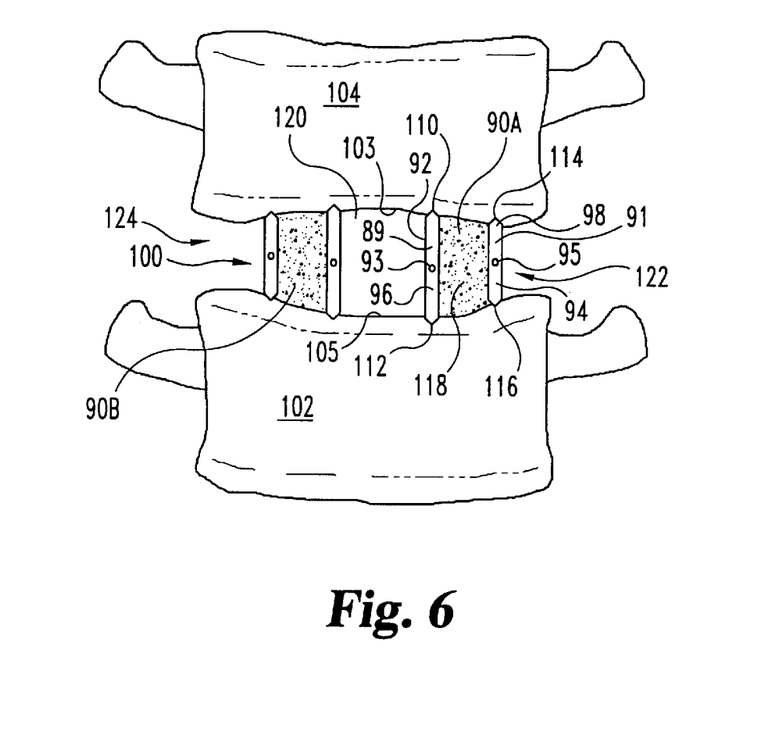
FIG. 6 is an anterior view of adjacent vertebrae illustrating the bi-lateral placement of a pair of implant assemblies provided in accordance with the present invention.

FIG. 6 is an anterior view of adjacent vertebrae illustrating the bi-lateral placement of a pair of implants according to the present invention. Implants 90A and 90B are inserted substantially parallel to each other into an intervertebral space 100. Referring to implant 90A, it can be seen that first strut 92 includes first bone-engaging portion 10 which bears against vertebral endplate 103 and an opposite bone-engaging portion 112 bearing against second vertebral endplate 105 and a first end 96 extending therebetween. Implant 90A also includes second strut 94, similar to first strut 92, includes a third bone-engaging portion 114 and an opposite fourth bone-engaging portion 116 and a first end 98 extending therebetween. Each bone-engaging portion 114 and 116, respectively, bear against respective vertebral endplates 105 and 103. An osteogenic material 118 is interposed between first strut 92 and second strut 94. Osteogenic material 118 hears against first and second endplates 103 and 105.

Implant 90A includes a first impact surface 89 formed in first end 96 disposed between first bone-engaging portion 110 and an opposite bone-engaging portion 112 Second strut 94 includes a second impact surface 91 formed in first end 98 disposed between third bone-engaging portion 114 and an opposite fourth bone-engaging portion 116. Impact surfaces 89 and 91 are provided to withstand the shear and force necessary to impact the respective implants into the disc space. For example impact surfaces 89 and 91 can defined thicken portions on first strut 92 and second strut 94. In preferred embodiments, impact surfaces 89 and 91 have sufficient thickness to withstand the impact force necessary to drive implant 90A into a intervertebral space with loss of integrity or deforming the molded implant configuration depicted by implant 90A including osteogenic material interposed between first and second strut 92 and 94. Impact surfaces 89 and 91 can define tool engaging apertures 93 and 95, respectively. It is understood by those skilled in the art that in addition to, or in place of, apertures 93 and 95, a variety of tool engaging structures can included in implant 90A, for example, slots, recessed areas, projections and additional apertures.

It can be seen from the illustrated embodiment that the bi-lateral placement of implants 90A and 90B can define an interior region 120. In preferred embodiments, interior region 120 can also be packed with a filler, such as an osteogenic material (not shown). The osteogenic material that is implanted into interior pocket 120 can be the same or can be different from the osteogenic material 118 provided or interposed between first and second struts 92 and 94. Similarly, after complete discectomy and appropriate bi-lateral placement of implants 90A and 90B, additional cavities 122 and 124 lateral of respective implants 90A and 90B can be provided to receive additional osteogenic material. This additional osteogenic material may be the same or may be different from the osteogenic material 118 interposed between first strut 92 and second strut 94.

FIG. 7 is a top view looking down on the superior endplate of vertebra 102 and implants 90A and 90B depicted in FIG. 6. Implant 90A is inserted from an anterior approach. First strut 92 has a second end 97 and second strut 94 has a second end 99, and each can include curved portions to ease the impact force necessary to embed the implant in the intervertebral space. Thus, first ends 96 and 98 are positioned anteriorly on vertebra 102, and second ends 97 and 99 are positioned posteriorly on vertebra 102. In alternative embodiments, when implants 90A and 90B are inserted from the posterior direction, second ends 97 and 98 can be provided similarly as discussed for first ends 96 and 98 to ease insertion of the implant in the anterior direction.

Figure 8:
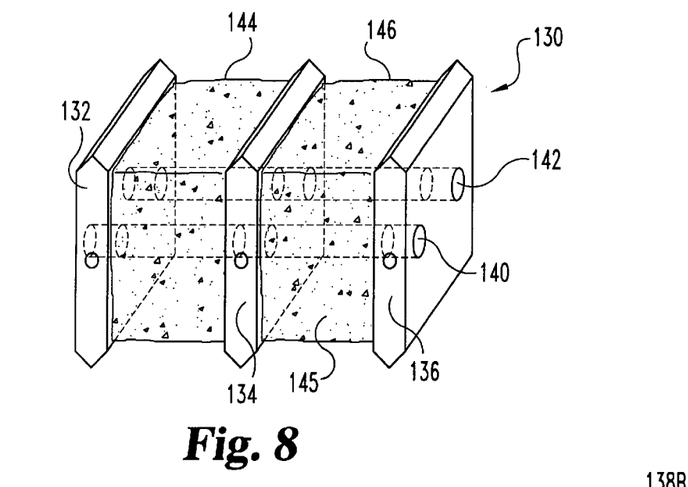
FIG. 8 is a perspective view of one embodiment of an implant assembly having three substantially parallel struts provided in accordance with the present invention.
Figure 9:
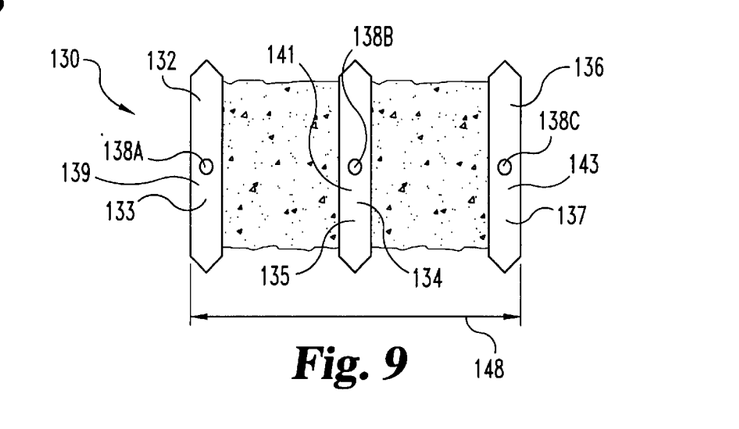
FIG. 9 is an elevated end view of the implant assembly illustrated in FIG. 8.

FIGS. 8 and 9 illustrate an alternative embodiment of an assembled implant according to the present invention. Implant 130 includes a first strut 132, a second strut 134 spaced from the first strut 132, and a third strut 136 spaced from the second strut 132. As with the previous implants 10, 40, 60 and 90A and 90B, each of the struts 132, 134, and 136 of implant assembly 130 include a pair of bone-engaging portions opposite each other and impact surfaces disposed between the opposite bone-engaging portions. Further, implant 130 includes a first cross-member 140 and a second cross-member 142 shown in dashed lines extending from strut 132 to strut 136. Cross-member 140 and/or cross-member 142 can be an integral cross-member extending from strut 132 through strut 134 and to strut 136. Alternatively, cross-member 140 and/or 142 can be an assembly of one or more cross-member sections. The cross-member sections can be substantially co-linear through implant 130. Alternatively, cross-member sections can be offset from each other as they extend from first strut 132, second strut 134 and to third strut 136. Implant 130 also includes a first internal area 144 defined by first strut 132 and second strut 134 and a second internal area 146 defined by second strut 134 and third strut 136. In preferred embodiments, internal areas 144 and 146 are filled with an osteogenic material 145. Preferably, this osteogenic material 145 is provided to adhere to the first strut, second strut, and/or third strut and cross-members 140 and 142. The osteogenic material will be discussed in more detail below.

In the illustrated embodiment, first strut 132, second strut 134, third strut 136 each include a first end 133, 135 and 137, respectively. Each first end 133, 135 and 137 defines respective impact surfaces 139, 141 and 143, respectively. First ends 133, 135 and 137 include one or more tool-engaging structures shown as apertures 138A, 138B and 138C. In alternative embodiments, implant 130 is not required to include either or both impact surfaces or tool-engaging structures on each strut. Therefore, implant 130 can include an impact surface and/or a tool-engaging structure in either of first strut 132, second strut 134 and/or third strut 136. Preferably, at least two struts, for example, first strut 132 and third strut 137, include impact surfaces and/or tool-engaging apertures.

In preferred embodiments, implant 130 is configured to be received within the intervertebral space on adjacent vertebrae. Thus, implant 130 can be provided in a variety of sizes, each size configured to be inserted between a-specific pair of adjacent vertebrae, for example, cervical, thoracic, or lumbar vertebrae. Furthermore, the implant assembly 130 can be provided so that the distance between first strut 132 and third strut 136, which is indicated by reference line 148, can be selected to equal $D_5$. The value for $D_5$ can be selected to place a portion of first strut 132 and third strut 136 on the peripheral ring structure apophysis of adjacent vertebrae.

Figure 10:
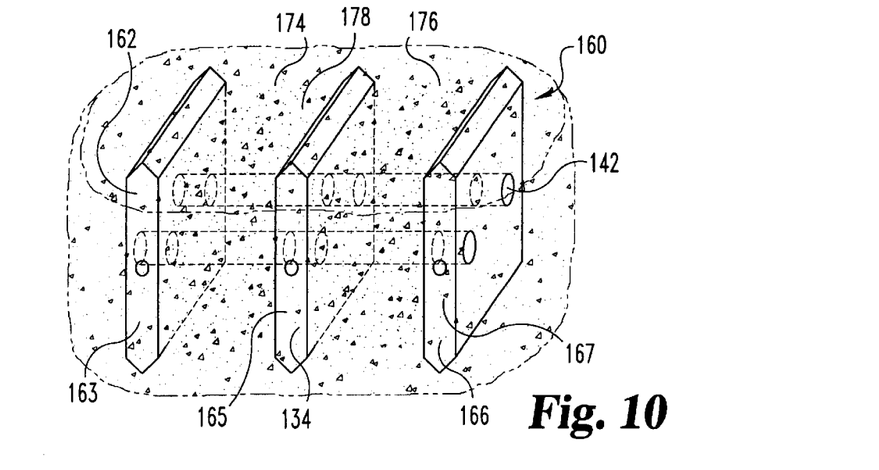
FIG. 10 is a perspective view of an implant embedded in a matrix of osteogenic material.

FIG. 10 is an illustration of still another embodiment of an implant assembly according to the present invention. Implant assembly 160, similar to implant assembly 130, includes three struts 162, 164 and 166. Struts 162, 164 and 166 define internal areas 174 and 176. An osteogenic material 178 can be received within internal areas 174 and 176. Furthermore, an osteogenic material 178 can be interposed between struts 162 and 164, and 164 and 166; in addition, osteogenic material 178 substantially encompasses first strut 162, second strut 164 and third strut 166. Thus, the respective struts can be substantially encased in the osteogenic material 178. In preferred embodiments, a portion of the first ends 163, 165 and 167 are available to engage an insertion tool. Therefore, in one embodiment, first ends 163, 165 and 167 extend beyond osteogenic material 178 to be available for attachment to an insertion tool (not shown).

Figure 11:
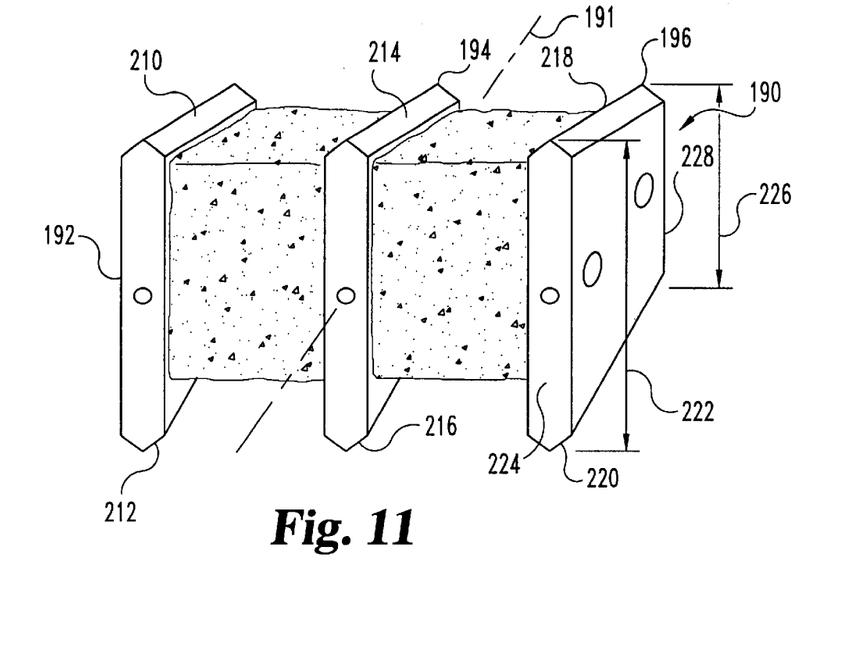
FIG. 11 is a perspective view of one embodiment of a lordotic implant assembly for use in the present invention.

FIG. 11 is a perspective illustration of another embodiment of a lordotic implant assembly according to the present invention. Implant assembly 190 defines a longitudinal axis 191 and includes a first strut 192, a second strut 194 and a third strut 196. Each of the respective struts 192, 194 and 196 include pairs of opposite bone-engaging portions 210 and 212, 214 and 216, and 218 and 220, respectively.

First strut 192, second strut 194, and third strut 196 can be provided as modular components for the implant assembly. Thus, the struts 192, 194 and 196 are provided in substantially the same configuration and dimensions. Therefore, opposing bone-engaging surfaces 210, 212, 214, 216, 218 and 220 on each respective strut are separated by the same distance. Further, each strut 192, 194 and 196 can be provided to correct lordotic deformities. For example, third strut 196 has a first end 224 and a second end 228. Adjacent to first end 224, first bone-engaging portion 218 and second bone-engaging portion 220 are separated by a distance represented by reference line 222, which is selected to equal $D_1$. At second end 228, first bone-engaging portion 218 is separated from second bone-engaging portion 220 by a distance represented by reference line 226, which is selected to equal $D_3$. Distance $D_1$ can be selected to be greater than $D_3$. In preferred embodiments, implant assembly 190 is provided to restore disc height and correct spinal lordosis.

Figure 12:
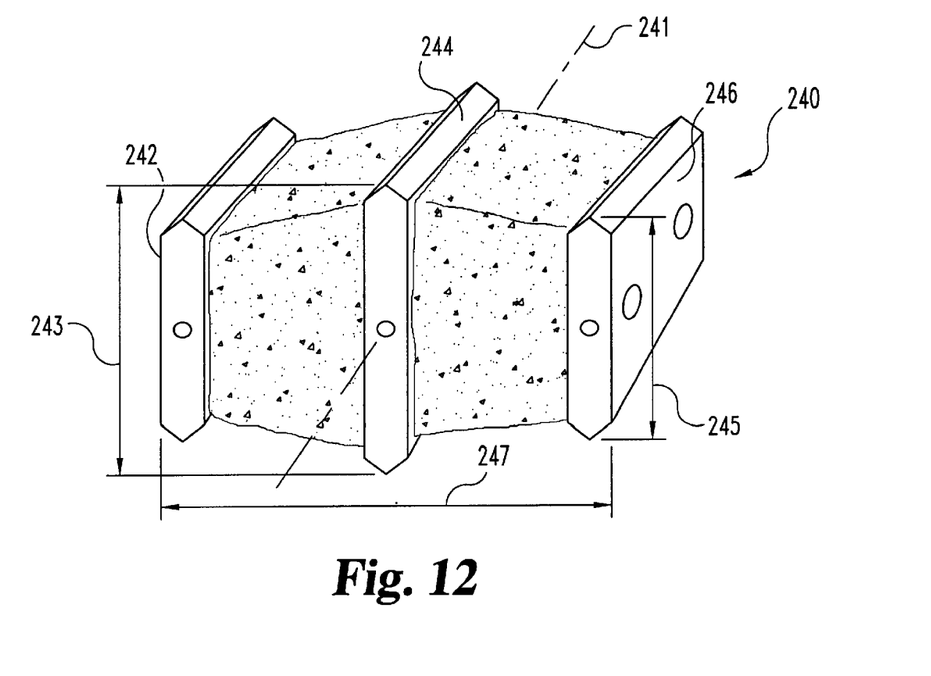
FIG. 12 is a perspective view of one embodiment of a domed implant assembly, for use with the present invention.

FIG. 12 is an illustration of one embodiment of a domed implant assembly according to the present invention. The implant assembly 240 defines a longitudinal axis 241. Implant assembly 240 includes a first strut 242, a second strut 244 and a third strut 246 extending in a direction substantially parallel to longitudinal axis 241. In the illustrated embodiment, first strut 242 and third strut 246 provide mirror images of each other. First strut 242 and third strut 246 are selected to have a first height transverse to longitudinal axis 241 and illustrated by reference line 245. Preferably the first height is selected to provide and maintain desired disc space height. Second strut 244 is provided to have a second height transverse to longitudinal axis 241 illustrated by reference line 243. In the illustrated embodiments, the first height is selected to be less than the second height. Preferably the first height is between about 5 mm and about 20 mm; more preferably, between about 10 mm to about 15 mm. The second height can be selected to be between about 5 mm and about 25 mm; more preferably between about 10 mm and about 20 mm.

As with the above-described implant assemblies, in implant 240, each strut 242, 244 and 246 includes opposite pairs of bone-engaging surfaces. Further, the bone-engaging surfaces can be provided substantially as described for the bone-engaging surfaces of the above implants 10, 40, 70, 90A, and 130.

Figure 13:
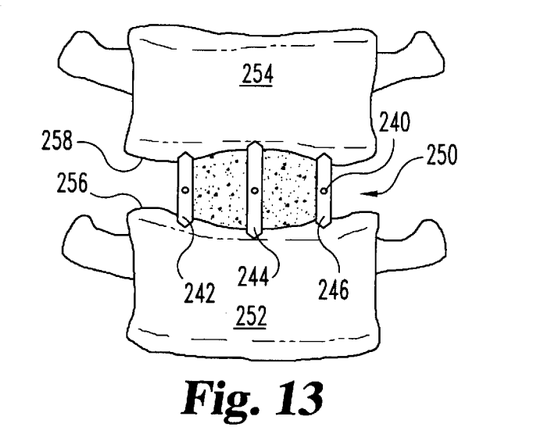
FIG. 13 is an anterior view of two adjacent vertebrae illustrating the placement of a domed implant assembly depicted in FIG. 12.

Referring additionally to FIG. 13, which illustrates the insertion of implant 250 between adjacent vertebrae 252 and 254, it can readily be seen that struts 242, 244, and 246 engage in opposing endplates 256 and 258 of vertebral bodies 252 and 254, respectively. First strut 242, second strut 244, and third strut 246 are illustrated as extending through vertebral endplates 256, 258 and into the cancellous bone tissue. It is also considered to be within the scope of the present invention to provide first strut 242, second strut 244, and third strut 246, which can be adapted to bear against opposing cortical bone endplates 256 and 258.

Implant 240 has a width transverse to longitudinal axis 241 and illustrated by reference line 247. Preferably the width is selected so implant 120 extends laterally across the end plates of opposing vertebrae so a portion of first strut 242 and a portion of third strut 246 engage the peripheral ring apophysis of the vertebrae.

Figure 14:
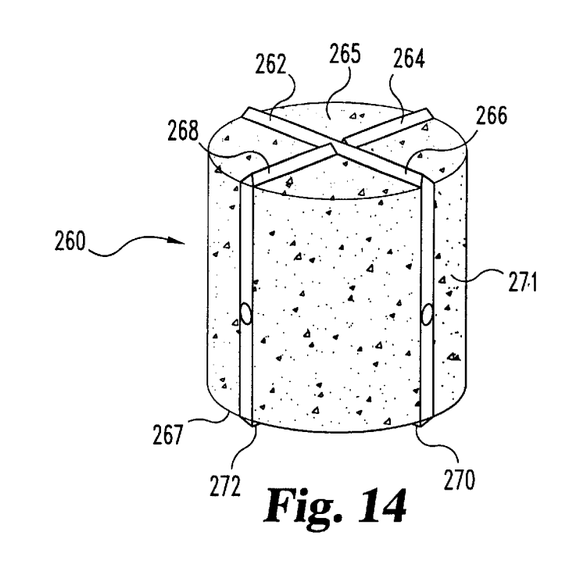
FIG. 14 is a perspective view of another embodiment of an implant assembly for use according to the present invention.
Figure 15:
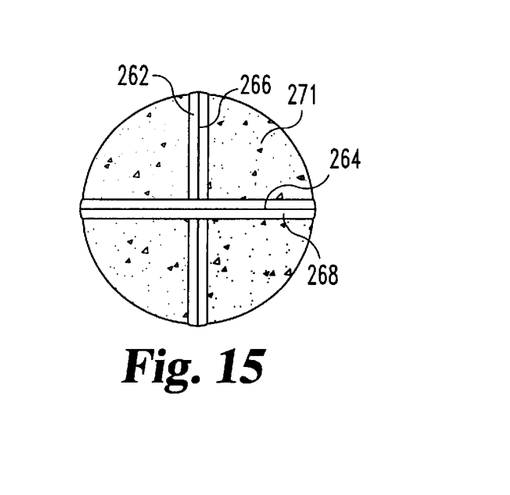
FIG. 15 is a top view of the implant assembly depicted in FIG. 14.
Figure 16:
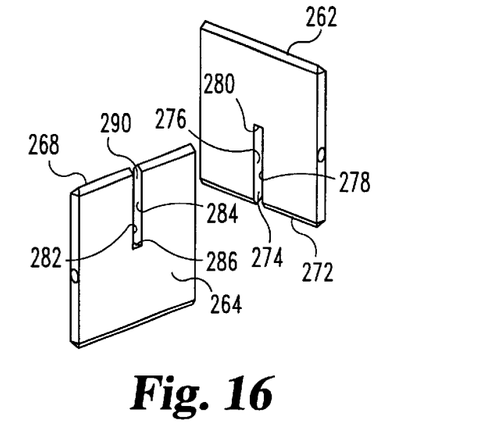
FIG. 16 is an exploded view of the implant assembly depicted in FIG. 14.

FIGS. 14–16 illustrate an alternative embodiment of an implant assembly according to the present invention. Implant assembly 260 includes at least a first strut 262 and a second strut 264 substantially orthogonal to each other. Each strut 262 and 264 includes first bone-engaging portions 266 and 268, respectively, and opposite second bone-engaging portions 270 and 272, respectively. A moldable osteogenic material 271 substantially encases struts 262 and 264.

In the illustrated embodiments, first strut 262 and 264 are adapted to matingly interengage each other, as illustrated in FIG. 16. First strut 262 includes a slot 274 extending from second bone-engaging portion 272. Slot 274 includes a first internal wall 276, an opposing second internal wall 278 and an end wall 280 disposed therebetween. Similarly, second strut 264 includes a slot 290 extending from first bone-engaging portion 268. Slot 290 includes a first internal wall 282, an opposing second internal wall 284 and end wall 286 disposed therebetween. When assembled, slot 280 of first strut 262 receives a portion of second strut 264. Concomitantly, second slot 290 and second strut 264 receive a portion of first strut 262.

First strut 262 and second strut 264 can be obtained from slices of cortical bone and exhibit a substantially rectangular shape having a height defined by opposite bone-engaging portions 266, 272 and 268, 278 of between about 5 mm to about 80 mm. In one form, implant assembly 260 can be sized to be inserted in a disc space between adjacent vertebrae. The height of first strut 262 and second strut 264 can be selected to be between about 5 mm and about 20 mm. In another form, implant assembly 260 can be sized to replace a vertebral body. When thus configured first strut 262 and second strut 264 can have a height selected between about 50 mm and 80 mm.

First strut 262 and second strut 264 interengage to provide an upper surface 265 and a lower surface 267 that are substantially planar. Alternatively, assembled implant 260 can be adapted to exhibit an upper surface 265 and lower surface that matingly engage and bear against the opposing endplates of vertebrae adjacent the implantation site. For example in alternative forms, implant 260 can exhibit a domed upper surface 265 and/or lower surface 267 configured similar to the upper and lower surfaces of implant 240. Still further, implant 260 can exhibit a lordotic configuration as illustrated for implant 290. Implant 260 can also be described as providing a substantially cylindrical implant configuration. However, it is considered to be within the scope of this invention to provide implant 260 in a wide variety of configurations. Preferably implant 260 is provided in a shape resembling the nucleus pulposa. Other exemplary configurations include spherical, ovoidal, frustoconical, and kidney shaped.

Figure 17:
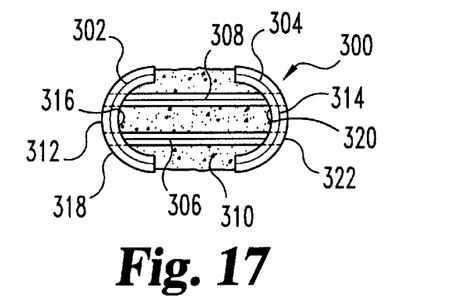
FIG. 17 is a top view of one embodiment of an implant assembly having curved struts for use in the present invention.
Figure 18:
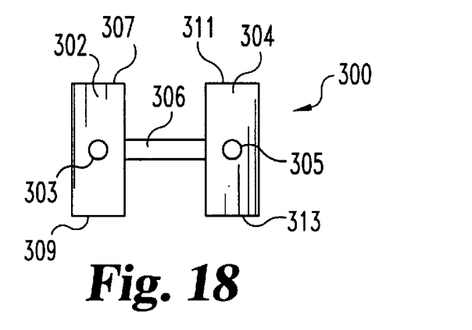
FIG. 18 is an elevated end view of the implant assembly depicted in FIG. 17.
Figure 19:
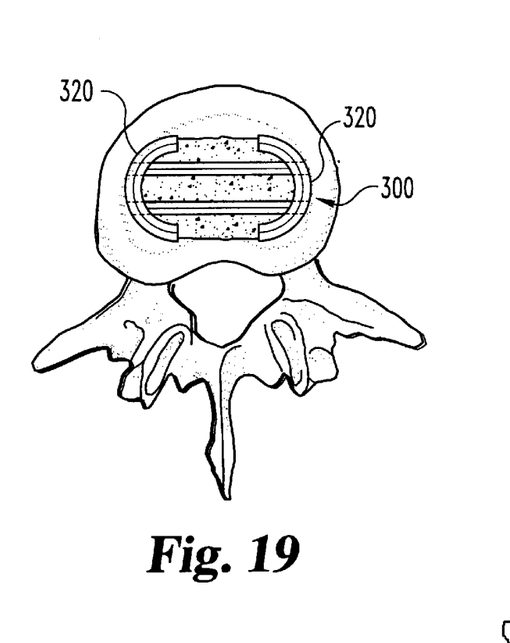
FIG. 19 is a top view of the implant assembly depicted in FIG. 17 positioned on a superior endplate of a lumbar vertebra.

FIGS. 17–19 illustrate another embodiment of an implant assembly according to the present invention. Implant assembly 300 includes a first-bone-derived strut 302 and a second bone-derived strut 304. Each of first strut 302 and second strut 204 includes pairs of opposite bone-engaging surfaces, 307, 309 and 311, 213, respectively. Implant 300 also includes at least one, preferably two, cross-members 306 extending between strut 302 and strut 304. An osteogenic material 310 is interposed between first strut 302 and second strut 304.

First strut 302 and second strut 304 each define a curved wall 312 and 314, respectively. Curved wall includes a first inner wall portion 316, which can be provided as a concave surface and an outer wall portion 318, which can be provided as a convex surface. Similarly, second curved wall portion strut 314 can also include an inner wall portion 320, provided as a concave surface and an outer wall portion 322 provided as a convex wall portion. In selected configurations, first and second struts 302 and 304 can be obtained from the diaphysis of long bones such that the respective concave surface portions are derived from and/or approximate the medullary canal. Further, first and second struts 302 and 304 can be provided with tool-engaging apertures 303 and 305, respectively. Implant 300 can be provided in a variety of dimensions for use in the intervertebral space between adjacent vertebrae including cervical vertebrae, thoracic vertebrae, and lumbar vertebrae. Preferably, first strut 302 and second strut 304 are spaced a distance from each other so that opposite pairs of bone-engaging surfaces 307, 309 and 311, 213 bear against the peripheral ring apophysis of the adjacent vertebral bodies, as illustrated in FIG. 19.

As has been disclosed above, the illustrated embodiments of the implants 10, 40, 70, 90A, 90B, 130, 160, 190, 240, 260, and 300 include cross-members. The cross-members are adapted to engage the respective first and second struts of the respective implants. The cross-members can be, but are not required to be, secured to opposing struts with an adhesive. Examples of additional engaging portions and methods of securing the cross-members to opposing struts are illustrated in FIGS. 20–23.

Figure 20:
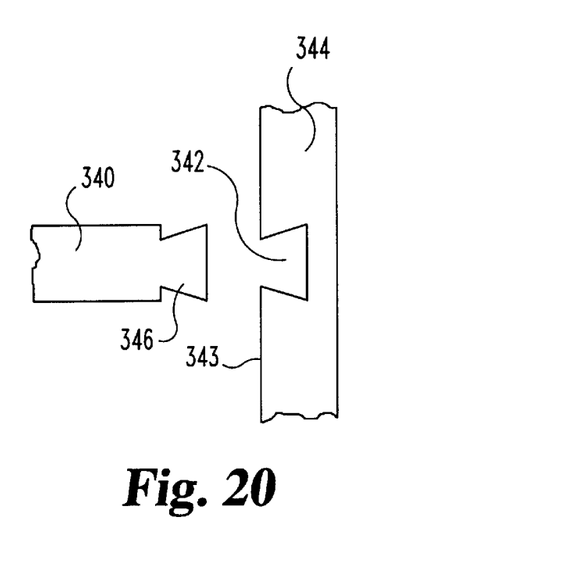
FIG. 20 is an exploded, partial view of an implant assembly of the present invention illustrating a dovetail connection of a cross-member and a strut.
Figure 21:
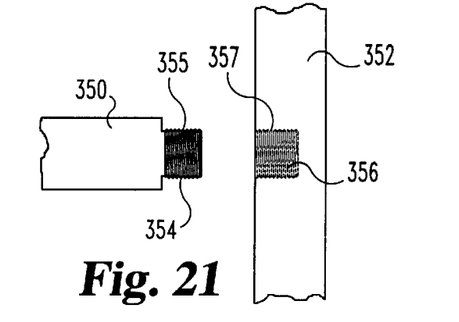
FIG. 21 is an exploded, partial view an implant assembly of the present invention illustrating a threaded connection of a cross-member and a strut.

In FIG. 20, cross-member 340 engages a groove such as dovetail slot 342 formed in a first wall surface 343 of strut 344. In the illustrated embodiment, a dovetail portion 346 matingly engages in the dovetail slot 342. For selected implant assemblies, for example, implant assemblies 130, 160, 190 and 240, strut 342 can include a second dovetail slot formed on the opposite wall surface. When thus provided, strut 342 can engage in two or more struts that can extend through the implant assemblies. FIG. 21 illustrates an alternative embodiment for the engagement of an illustrative cross-member 350 with a strut 352. Cross-member 350 includes an end portion 354 that engages in an aperture 356 formed in strut 352. In the illustrated embodiment, end portion 354 includes external threads 355 provided to threadedly engage in a threaded portion 357 of aperture 356.

Figure 22:
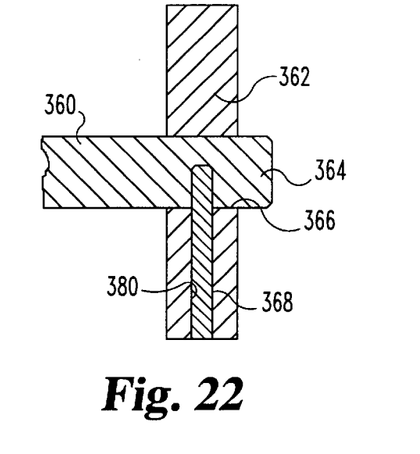
FIG. 22 is a partial sectional view of an implant assembly of the present invention illustrating a cross-member engaged to a strut using a keeper.

FIG. 22 illustrates another embodiment for an illustrative cross-member 360 to engage in a strut 362. An end portion 364 of cross-member 360 extends through an aperture 366 formed in strut 362. A retaining pin is received through a second opening 380 formed substantially orthogonal to aperture 366 in strut 362 and engages in end portion 364 of cross-member 360 to inhibit withdrawal of the end portion 364 from aperture 366.

Figure 23:
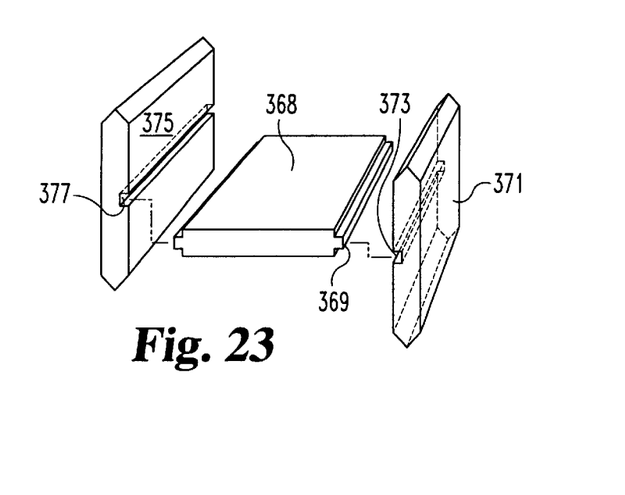
FIG. 23 is an exploded view of an alternative embodiment of an implant assembly having a single, planar cross-member.

FIG. 23 illustrates a cross-member configured as a single substantially planar structure. Cross-member 368 includes a tongue 369 adapted to be matingly received within a groove 373 formed in a first strut 371. A second strut 375 can provide a second groove 377 to receive a second tongue on cross-member 368 opposite tongue 369.

Figure 24:
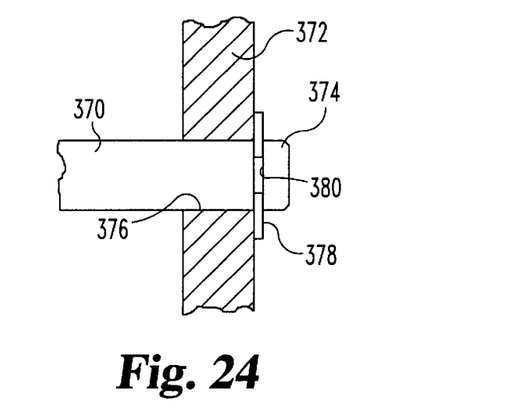
FIG. 24 is a partial sectional view of an alternative embodiment of an implant assembly of the present invention illustrating a cross-member engaged to a strut using a retaining ring.
Figure 25:
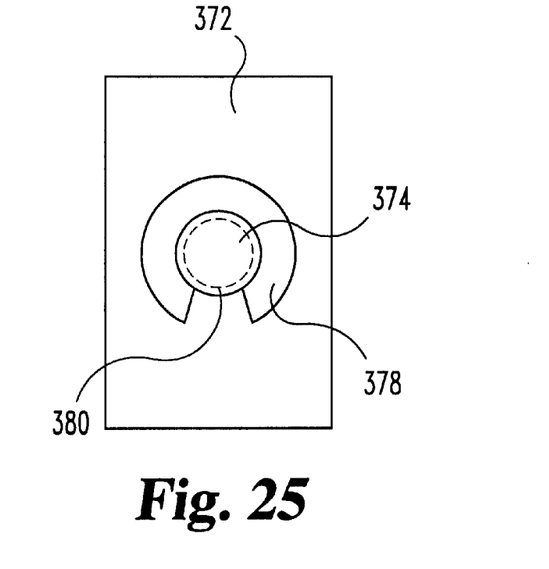
FIG. 25 is an elevated end view of the implant assembly depicted in FIG. 23.

FIGS. 24 and 25 illustrate still another embodiment of an engagement of a cross-member 370 with a strut 372. End portion 374 of cross-member 370 is received within an aperture 376 formed in strut 372. A retaining ring 378 matingly engages in a groove 380 formed in end portion 374 that extends beyond strut 372. This effectively inhibits withdrawal of cross-member 370 from aperture 376 of strut 372.

Referring now to FIG. 26, there is illustrated a schematic of a bone slice 400 cut from a long bone, such as a tibia bone or a femur bone. Bone slice 400 can be cut along reference lines 404 and/or 406 to provide a variety of bone-derived implants. For example, bone slice 400 can be divided into a central section 402, which can be used as an integrally formed implant potentially for insertion into adjacent vertebral bodies. Examples of integrally formed implants are described in U.S. Pat. No. 5,972,368 issued to McKay and in U.S. Pat. No. 5,033,438 issued to Bianchi. Bone portions 408 and 410, which remain after harvesting central portion 402, can be used to provide a first, second or third strut for the implant assemblies according to the present invention. Furthermore, bone portions 408 and/or 410 can be further partitioned to provide cross-members to extend from the first strut to a second strut or from a second strut to a third strut. It will also be observed that the illustrated bone portions 408 and 410 define first ends 412 and 414, respectively, that are thicker than the opposite second ends 416 and 418, respectively.

The osteogenic material is selected to adhere to the implant assembly. Further, osteogenic material preferably includes as a demineralized bone matrix and optionally a carrier, such as a gelatin substance. The demineralized bone matrix can be provided in the form of a powder, paste or gel. When provided as a powder, the osteogenic material can be reconstituted with sterile water, saline, glycerin or other physiological solutions. The reconstituted material is molded about the implant assembly. An osteogenic material can be applied to the implant assembly by the surgeon during surgery or the spacer assembly may be supplied with the composition pre-applied. In such cases, the osteogenic composition may be stabilized for transport and storage. Preferably the osteogenic material is provided as a putty that can be retained in and about the implant assembly. The osteogenic putty is a moldable, flowable material that sets up to a semi-rigid form at about body temperature. The implant assembly with the osteogenic material is then inserted into a prepared disc space. The osteogenic material can also include a reinforcement such as bone chips, preferably cortical bone chips. Examples of osteogenic material suitable for use with this invention include, but are not limited to: OSTEOFIL, which is commercially available from Regeneration Technologies, Inc. of Alachua, Fla.; GRAFTON CRUNCH available from Osteotech of Eatontown, N.J. and ALLOMATRIX, available from Allosource of Denver, Colo.

The term osteogenic composition used here means virtually any osteo conductive or osteo inductive material that promotes bone growth or healing including natural, synthetic and recombinant proteins, hormones and the like. The osteogenic materials used in this invention preferably comprise a therapeutically effective amount of a bone inductive factor such as a bone morphogenetic protein in a pharmaceutically acceptable carrier. Examples of factors include recombinant human bone morphogenic proteins (rhBMPs) rhBMP-2, rhBMP-4 and heterodimers thereof. However, any bone morphogenetic protein is contemplated including bone morphogenetic proteins designated as BMP-1 through BMP-13, which are available from Genetics Institute, Inc., Cambridge, Mass. All osteoinductive factors are contemplated whether obtained as above or isolated from bone.

The present invention contemplates modifications of the implant and methods as would occur to those skilled in the art. It is also contemplated that processes embodied in the present invention can be altered, rearranged, substituted, deleted, duplicated, combined, or added to other processes as would occur to those skilled in the art without departing from the spirit of the present invention. Further it is understood that above described bone-derived components are individual modular units that can be combined and/or assembled into additional configurations not specific illustrated in the figures included herewith. All of the individual bone-derived components can be provided in the varying sizes and include any of the specific surface features and structures associated with the embodiments illustrated or described herein. In addition, the various stages, steps, procedures, techniques, phases, and operations within these processes may be altered, rearranged, substituted, deleted, duplicated, or combined as would occur to those skilled in the art. All publications, patents, and patent applications cited in this specification are herein incorporated by reference as if each individual publication, patent, or patent application was specifically and individually indicated to be incorporated by reference and set forth in its entirety herein.

Further, any theory of operation, proof, or finding stated herein is meant to further enhance understanding of the present invention and is not intended to make the scope of the present invention dependent upon such theory, proof, or finding.

While the invention has been illustrated and described in detail in the drawings and foregoing description, the same is considered to be illustrative and not restrictive in character, it is understood that only the preferred embodiments have been shown and described and that all changes and modifications that come within the spirit of the invention are desired to be protected.

What is claimed is:

1. An implant for promoting bone fusion between adjacent vertebral bodies, said implant having an exterior surface, a longitudinal axis and comprising an assembly of cortical bone-derived components, said components comprising:

a first strut having a first bone-engaging portion, an opposite second bone-engaging portion, a first impact surface disposed therebetween in a plane positioned substantially orthogonal to the longitudinal axis, and a first end opposite the first impact surface;

a second strut spaced from said first strut, said second strut having a third bone-engaging portion, an opposite fourth bone-engaging portion, a second impact surface disposed therebetween in a plane positioned substantially orthogonal to the longitudinal axis, and a second end opposite the second impact surface, said second strut in cooperation with said first strut defining an internal space, wherein the first strut and the second strut each include an aperture opening into the internal space and wherein the first end of the first strut and the second end of the second strut each include a curved surfacing curving from the internal space to the external surface;

an elongate cross-member extending from the first strut to the second strut and including a first end engaged within the first aperture of the first strut and a second end engaged within the aperture of the second strut;

an osteogenic material interposed between the first and second strut, said osteogenic material provided to be adherent to at least one of the first strut, the second strut and the cross-member and adapted to be moldable to provide a semi-rigid shaped component; and wherein said first and second impact surfaces define planar surfaces positioned substantially parallel to the elongate cross-member and each planar surface comprising a tool engaging aperture.

2. The implant of claim 1 wherein the osteogenic material includes cancellous bone particles.

3. The implant of claim 1 wherein the osteogenic material hardens at a temperature between about 35° C. and about 40° C.

4. The implant of claim 1 wherein the osteogenic material is capable of supporting a portion of a compressive load exerted by adjacent vertebral bodies without significant deformation of the shaped component when said implant is received within the intervertebral space.

5. A method of treating a spinal deformity, said method comprising;

surgically implanting the implant of claim 1 into a prepared disc space.

6. The implant of claim 1 wherein the first end has a height $D_1$ measured transverse to the longitudinal axis and the first impact surface has a height $D_3$ also measured transverse to the longitudinal axis, wherein $D_1$ is greater than $D_3$.

7. The implant of claim 6 wherein the second end has a height $D_2$ measured transverse to the longitudinal axis and second impact surface has a height $D_4$ also measured transverse to the longitudinal axis, wherein $D_2$ is greater than $D_4$.

8. The implant of claim 1 wherein the cross-member is positioned to lie transverse to the longitudinal axis and extend through the interior space.

9. The implant of claim 1 wherein said first strut and said second strut are adapted to minimize stress shielding of the osteogenic material when the implant assemble is received within the intervertebral space.

10. The implant of claim 1 wherein the first, second, third and fourth bone-engaging portions include anti-expulsion structures.

11. The implant of claim 1 wherein the first and second struts are sized to provide an implant suitable to be implanted between opposing endplates of adjacent lumbar vertebrae.

12. The implant of claim 1 wherein the first and second struts are sized to provide an implant suitable to be implanted between opposing endplates of adjacent cervical vertebrae or adjacent thoracic vertebrae.

13. The implant of claim 1 wherein the first strut and said second strut each have a height, transverse to the longitudinal direction, between about 5 mm and about 20 mm.

14. The implant of claim 1 wherein the first strut and the second strut are adapted to engage in opposing vertebral endplates and facilitate lordosis.

15. The implant of claim 1 wherein the first bone-engaging portion is separated from the second bone-engaging portion by a distance $D_1$ and the third bone-engaging portion is separated from the fourth bone-engaging portion by a distance $D_2$ less than $D_1$.

16. The implant of claim 15 wherein $D_1$ is between about 5 mm and about 20 mm.

17. The implant of claim 7 wherein $D_1$ is greater than $D_2$ and $D_3$ is greater than $D_4$.

18. The implant of claim 1 wherein the first strut defines a substantially planar first wall portion and the second strut defines a substantially planar second wall portion positioned to lie substantially parallel to said first wall portion.

19. The implant of claim 1 wherein the aperture includes an internally threaded portion and the proximal end of the cross-member includes external screw threads to threadedly engage said internally threaded portion.

* * * * *